United States Patent [19]

Stevens

[11] Patent Number: 4,882,360

[45] Date of Patent: * Nov. 21, 1989

[54] PROCESS FOR PRODUCING ALCOHOLS FROM SYNTHESIS GAS

[75] Inventor: Rex R. Stevens, Midland, Mich.

[73] Assignee: The Dow Chemical Company, Midland, Mich.

[*] Notice: The portion of the term of this patent subsequent to Jun. 21, 2005 has been disclaimed.

[21] Appl. No.: 202,755

[22] Filed: Jun. 6, 1988

Related U.S. Application Data

[60] Division of Ser. No. 903,878, Sep. 3, 1986, Pat. No. 4,752,622, which is a continuation of Ser. No. 636,000, Jul. 30, 1984, abandoned.

[51] Int. Cl.$^4$ .............................................. C07L 27/06
[52] U.S. Cl. ................................... 518/714; 562/220
[58] Field of Search ......................................... 518/714

[56] References Cited

U.S. PATENT DOCUMENTS

| | | |
|---|---|---|
| 1,201,850 | 10/1916 | Mittasch et al. |
| 1,558,559 | 10/1925 | Mittasch et al. |
| 1,859,244 | 5/1932 | Patart |
| 2,490,488 | 12/1949 | Stewart |
| 2,539,414 | 1/1951 | Frankenburg |
| 2,821,537 | 1/1958 | Rottig |
| 2,960,518 | 11/1960 | Peters |
| 3,842,113 | 10/1974 | Ichikawa et al. |
| 3,842,121 | 10/1974 | Ichikawa |
| 3,850,840 | 2/1972 | Aldridge et al. |
| 3,928,000 | 12/1975 | Child et al. |
| 4,096,164 | 6/1978 | Ellgen et al. |
| 4,151,190 | 4/1979 | Murchison et al. |
| 4,151,191 | 4/1979 | Happel et al. |
| 4,168,276 | 9/1979 | Finch |
| 4,177,202 | 12/1979 | Chang et al. |
| 4,199,522 | 4/1980 | Murchison et al. |
| 4,260,553 | 4/1981 | Happel et al. |
| 4,261,864 | 4/1981 | Hargis |
| 4,298,354 | 11/1981 | Hardman et al. |
| 4,380,589 | 4/1983 | Murchison et al. |
| 4,405,815 | 9/1983 | Keim et al. |
| 4,440,668 | 4/1984 | Chang et al. |
| 4,451,579 | 5/1984 | Lemanski et al. |
| 4,459,369 | 7/1984 | Passariello |
| 4,478,954 | 10/1984 | Connolly et al. |
| 4,511,674 | 4/1985 | Pedersen et al. |
| 4,513,096 | 4/1985 | Connolly et al. |
| 4,513,100 | 4/1985 | Fattore et al. |
| 4,544,673 | 10/1985 | Lemanski et al. |
| 4,607,055 | 8/1986 | Grazioso et al. |
| 4,607,056 | 8/1986 | Grazioso et al. |
| 4,616,040 | 10/1986 | Grazioso et al. |
| 4,661,525 | 4/1987 | Grazioso et al. |
| 4,675,344 | 6/1987 | Conway et al. |
| 4,749,724 | 6/1988 | Quarderer et al. |
| 4,752,622 | 6/1988 | Stevens |
| 4,752,623 | 6/1988 | Stevens et al. |

FOREIGN PATENT DOCUMENTS

| | | |
|---|---|---|
| 251483 | 7/1925 | Canada |
| 119609 | 9/1984 | European Pat. Off. |
| 149255 | 7/1985 | European Pat. Off. |
| 149256 | 7/1985 | European Pat. Off. |
| 1058797 | 3/1954 | France |
| 170023 | 9/1984 | Japan |
| 254760 | 7/1926 | United Kingdom |
| 1501892 | 2/1978 | United Kingdom |
| 2065490 | 7/1981 | United Kingdom |
| 2151616 | 7/1985 | United Kingdom |

OTHER PUBLICATIONS

British Coal Corp. letter to the EPO dated Jul. 6, 1987.
Anderson, R. B. et al., "Fischer-Tropsch Synthesis," Engineering and Process Development, *Industrial & Engineering Chemistry*, vol. 44, No. 2, pp. 391-401 (1952).
Anderson, R. B. et al., "Synthesis of Alcohols by Hydrogenation of Carbon Monoxide," Industrial and Engineering Chemistry, vol. 44, No. 10, pp. 2418, 2424 (1952).
*A Critical Analysis of Recent Advances in CO-H$_2$ Catalysis*, prepared by Catalytica Assoc., Inc., Santa Clara, CA 95051, Multiclient Study No. 1124, Jun., 1980 (excerpted).
Tatsumi et al., *Chemistry Letters*, Chemical Society of Japan (5), pp. 685-688 (1984).
Diffenbach, R. A. et al., *Synthesis Gas Conversion to Liquid Fuels Using Promoted Fused Iron Catalysts*, DOE/PETC/TR-81/3 (Sep., 1981).
Greene, C.E.P. (Aug., 1982), pp. 46-51.
Kummer, J. T. et al., vol. 73, pp. 564-569 (Feb., 1951).
Kummer, J. T. et al., vol. 75, pp. 5177-5183 (Nov. 5, 1953).

*Primary Examiner*—Howard T. Mars

[57] ABSTRACT

A process for making alcohols comprising contacting a mixture of hydrogen and carbon monoxide with a catalyst comprising:
(1) as a first component, at least one element selected from the group consisting of molybdenum and tungsten in free or combined form;
(2) as a second component, at least one element selected from the group consisting of iron, cobalt and nickel in free or combined form;
(3) as a third component, a promoter comprising an alkali or alkaline earth element in free or combined form; and optionally
(4) as a fourth component, a support;
to form an alcohol fraction boiling in the range of motor gasoline in at least 20 percent $CO_2$ free carbon selectivity.

10 Claims, No Drawings

PROCESS FOR PRODUCING ALCOHOLS FROM SYNTHESIS GAS

This is a divisional of application Ser. No. 903,878, filed Sept. 3, 1986, which is now issued as U.S. Pat. No. 4,752,622 which is a continuation of Ser. No. 636,000, filed July 30, 1984 which is now abandoned.

FIELD OF THE INVENTION

This invention relates to a Fischer-Tropsch process for making alcohols and describes the catalyst composition and conditions of the process.

BACKGROUND OF THE INVENTION

Almost as old as the Fischer-Tropsch process for making hydrocarbons is the Fischer-Tropsch process for making alcohols. The reaction is carried out by passing a mixture of carbon monoxide and hydrogen over a catalyst for the hydrogenation of the carbon monoxide. A typical review article is R. B. Anderson et al., *Industrial and Engineering Chemistry*, Vol. 44, No. 10, pp. 2418–2424. This paper lists a number of catalysts containing zinc, copper, chromium, manganese, thorium, iron, occasionally promoted with alkali or other materials for making various alcohols. The authors state that ethyl alcohol is a major constituent, the yield of methanol is usually very small and a tentative summary of factors favoring the production of alcohols are high pressure, low temperature, high space velocity, high recycle ratio and carbon monoxide-rich synthesis gas.

Molybdenum is known to be catalytic for the Fischer-Tropsch process and is taught in U.S. Pat. Nos. 4,151,190 and 4,199,522 which are incorporated herein by reference. The references describe some of the herein used catalysts but do not teach that the catalyst is useful for making commercially significant quantities of alcohols.

U.S. Pat. No. 2,490,488 discloses that molybdenum sulfide methanation catalysts acquire Fischer-Tropsch activity when promoted with an alkaline compound of an alkali metal. The example of the invention shows a 30 percent selectivity to $C_3+$ hydrocarbons and oxygenates. Of this 30 percent, no more than 44 percent boils near or above 65° C. the boiling point of methanol. Accordingly the maximum possible alcohol selectivity is no more than 13.2 percent (44 percent of 30 percent).

U.S. Pat. No. 2,539,414 describes a Fischer-Tropsch process with molybdenum carbide-catalysts. It teaches that the catalyst may be used to form oxygenates and at column 3, lines 66–71 teaches that one might get alcohols or hydrocarbons by varying the conditions.

G. T. Morgan et al., *J. Soc. Chem. Ind.*, Vol. 51, Jan. 8, 1932 pp. 1T–7T, describe a process for making alcohols with chromium/manganese oxide catalysts promoted with alkali.

A number of references teach production of alcohols using rhodium catalysts. Some of these contain molybdenum as an optional ingredient. U.S. Pat. No. 4,014,913 discloses a catalyst containing rhodium and thorium or uranium and iron or molybdenum or tungsten for the production of ethanol. U.S. Pat. No. 4,096,164 discloses the use of rhodium in combination with molybdenum or tungsten. Example A discloses that use of a molybdenum-on-silica catalyst yielded 4.4 percent oxygenates.

EP0 application 81-33,212 (Chemical Abstracts 96: 51,800a) discloses a similar process using rhodium in combination with one or more of a long list of metals which includes molybdenum.

EPO application 79-5,492 (Chemical Abstracts 92: 166,257b), Hardman et al., discloses the production of alcohols using a 4-component catalyst. The first component is copper, the second is thorium, the third an alkali metal promoter and the fourth a long list of metals one of which is molybdenum. Chemical Abstracts 96: 106,913x, Diffenbach et al., disclose a nitrided iron catalyst which is promoted with molybdenum for making alcohols from synthesis gas.

All of the aforementioned references are hereby incorporated by reference.

U.S. patent application No. 476,674, filed Mar. 18, 1983 and U.S. patent application No. 622,029, filed June 18, 1984, which are incorporated herein by reference disclose a process for making mixed alcohols by contacting hydrogen and carbon monoxide with a catalyst containing, molybdenum, tungsten or rhenium in combination with an alkali(ne earth) promoter and optionally a support. The Applicants disclose that other metals such as iron, nickel or cobalt may also be combined with their catalyst but do not teach advantageous results for the combination.

While this process is an advance over the art it would be more advantageous if it were possible to decrease the percentage of methanol in the mixed alcohols made. Methanol has been blamed for difficulties when blended into motor gasolines. Accordingly there is some advantage to varying or minimizing the ratio of $C_1$ to $C_2+$ alcohols in the mixed alcohols made by the processes of SN 476,674 and SN 622,029.

U.S. Application, filed on even date herewith Ser. No. 4,675,344, which is incorporated herein by reference, discloses a method for adjusting the ratio of $C_1$ to $C_2+$ alcohols in the processes of SN 476,674 and SN 622,029 by adjusting the addition rate of a sulfur releasing substance to the $H_2/CO$ feed. Increasing the sulfur level decreases the $C_1$ to $C_2+$ alcohols ratio. Concurrently, however, increasing the sulfur in the feed also decreases the activity or weight of alcohols per unit weight of catalyst per unit of time. It would be more desirable to lower the $C_1$ to $C_2+$ ratio without lowering the activity of the catalyst. Use of sulfur releasing substances also requires that sulfur be removed from the mixed alcohols product.

To make a commercially significant alcohol process, one must use a catalyst and conditions which are highly efficient. To be efficient the catalyst must yield a high ratio of mass of product per given mass of catalyst in a given period of time. The catalyst must be stable and active for long periods of time between regenerations. This may be particularly difficult to accomplish when the $H_2/CO$ ratio of the feed gas is low, such as less than 2 to 1. Ideally the catalyst will be highly selective to a commercial product to avoid purification or removal and disposal of by-products and to avoid separation into two or more product streams.

When the mixed alcohols product is to be used as a fuel replacement or a fuel additive, it may be desirable that the ratio of $C_1$ to $C_2+$ alcohols be no greater than a certain amount. As used in this Application, the ratio of $C_1$ to $C_2+$ alcohols means the weight ratio of methanol to higher alcohols such as ethanol, propanols, butanols, etc., taken as a whole. This number may be calculated by determining the weight fraction of methanol in the mixed alcohols. When the weight fraction of methanol is x, the ratio of $C_1$ to $C_2+$ alcohols is $$\frac{x}{1-x}.$$

Since $C_2+$ alcohols, in its broadest definition refers to alcohols which are not detected by conventional analytical techniques, a more meaningful approximation of the $C_1$ to $C_2+$ ratio of methanol to higher alcohols includes only the $C_2$-$C_5$ alcohols in the definition of $C_2+$ alcohols. Alcohols bound as esters or ethers are not included in either the $C_1$ or $C_2+$ numbers.

OBJECTS OF THE INVENTION

It is an object of this invention to prepare alcohols from $H_2$/CO synthesis gas. It is a preferred object of this invention to make a high yield of alcohols with a catalyst which is selective to alcohols boiling in the range of motor gasoline and that is stable, particularly at low $H_2$/CO ratios, and active over long periods of time. It is a most preferred object of this invention to obtain a mixed alcohol fraction with a lower $C_1$ to $C_2+$ alcohols ratio than obtainable with a straight molybdenum catalyst without lowering the activity of the catalyst and without increasing the sulfur level in the product stream.

SUMMARY OF THE INVENTION

One or more of the objects of the invention may be effected by a process for making alcohols comprising contacting a mixture of hydrogen and carbon monoxide with a catalyst comprising:
(1) as a first component at least one element selected from the group consisting of molybdenum and tungsten in free or combined form;
(2) as a second component at least one element selected from the group consisting of iron, cobalt and nickel in free or combined form;
(3) as a third component, a promoter comprising an alkali or alkaline earth element in free or combined form; and optionally as a fourth component
(4) a support; to form an alcohol fraction boiling in the range of motor gasoline in at least 20 percent $CO_2$ free carbon selectivity.

It is a feature of this invention, that high yields and selectivity may be obtained without the use of rhodium, copper, ruthenium or zinc. An advantage of the invention is that high production rates may be obtained at high selectivities. Under preferred conditions, these catalysts may yield high $C_1$-$C_5$ alcohol productivity. Up to about 1.4 weight units $C_1$-$C_5$ alcohol/hr/weight unit of catalyst may be achieved. With cobalt, iron or nickel added to the catalyst the ratio of $C_1$ to $C_2$-$C_5$ alcohols may be considerably lower than for the same catalyst without the iron, nickel or cobalt, while still retaining the high catalyst activity and low sulfur level mixed alcohol fraction. Because of the high selectivity, complex purification steps may be avoided and the alcohol product may have a low acid content and have a high octane blending value. This may permit blending into motor fuels without elaborate processing. In addition, contrary to what is experienced with a molybdenum catalyst as one increases the temperature the ratio of $C_1$ to $C_2$-$C_5$ alcohols may stay the same or may even decrease.

DETAILED DESCRIPTION OF THE INVENTION

The hydrogen and carbon monoxide required for this process can be obtained by methods known in the art. Examples are gasification of hydrocarbonaceous materials such as coal, high specific gravity oils, or natural gas; as a by-product of partial combustion cracking of hydrocarbons; by steam reforming of liquid or gaseous hydrocarbons; through the water-gas shift reaction; or some combination of these. The two components may also be generated separately and combined for the subject reaction. The molar ratio of hydrogen to carbon monoxide in the feed gas which contacts the catalyst ranges generally from about 0.25 to about 100, preferably from about 0.5 to about 5 and most preferably from about 0.7 to about 3. A most preferred range of from about 0.7 to about 1.2 holds for unsupported Co/$MoS_3$ catalysts.

Generally, the selectivity to alcohols is dependent on the pressure. In the normal operating ranges, the higher the pressure at a given temperature, the more selective the process will be to alcohols. The minimum contemplated pressure is about 500 psig (3.55 MPa). The preferred minimum is about 750 psig (5.27 MPa) with about 1,000 psig (7.00 MPa) being a more preferred minimum. While about 1,500 psig (10.45 MPa) to about 4,000 psig (27.7 MPa) is the most desirable range, higher pressures may be used and are limited primarily by cost of the high pressure vessels and compressors needed to carry out the higher pressure reactions. A typical maximum is about 10,000 psig (69.1 MPa) with about 5,000 psig (34.6 MPa) a more preferred maximum.

The selectivity to alcohols is also a function of temperature and is interrelated with the pressure function. The minimum temperature used is governed by productivity considerations and the fact that at temperatures below about 200° C. volatile catalytic metal carbonyls may form. Accordingly, the minimum temperature is generally around 200° C.

For a given catalyst, at a constant pressure, as the temperature increases, the selectivity to alcohols decreases. A preferred maximum temperature is about 400° C. A more preferred maximum is about 350° C. However, the most preferred range of operation is from about 240° C. to about 325° C.

The $H_2$/CO gas hourly space velocity (GHSV) is a measure of the volume of hydrogen plus carbon monoxide gas at standard temperature and pressure passing a given volume of catalyst in an hour's time. This may range from about 100 to about 20,000 hour$^{-1}$ and preferably from about 2,000 to about 5,000 hour$^{-1}$. Selectivity to the alcohols generally increases as the space velocity increases. However, conversion of carbon monoxide decreases as space velocity increases.

Preferably at least a portion of the unconverted hydrogen and carbon monoxide in the effluent gas from the reaction, more preferably after removal of product alcohols, water and carbon dioxide formed and even more preferably any hydrocarbons formed, may be recycled to the reaction. The amount of recycle is expressed as the recycle ratio which is the ratio of moles of gases in the recycle stream to the moles of gases in the fresh feed stream. A recycle ratio of zero is within the scope of the invention with at least some recycle preferred. A recycle ratio of at least about one is more preferred and at least about three is most preferred.

With preferred catalysts and under preferred conditions of temperatures, pressures, $H_2$/CO ratio, GHSV and recycle ratio, about 0.1 weight units of alcohols or more per hour may be formed per weight unit of catalyst. Under the more preferred conditions of about 310°

C., 1500 psig (10.45 MPa), 3800 hour$^{-1}$ and a H$_2$/CO ratio of about 1:1, with a 2Mo/Co catalyst, about 0.3 weight units of alcohol or more per hour per weight unit of catalyst may be obtained. Under the most preferred conditions of about 340° C., 3000 psig (20.9 MPa), a GHSV of 13,000 and a H$_2$/CO ratio of 1.1; with a 2Mo/Co catalyst about 1.4 weight units of alcohols or more per hour per weight unit of catalyst may be obtained.

Under preferred conditions, alcohols may be obtained in about an 85 percent CO$_2$ free carbon selectivity. The CO$_2$ free carbon selectivity is defined as 100 times the moles of carbon present in a product fraction divided by the total moles of carbon in all products which are not CO$_2$ or unconverted feed. For example, if one mole of ethanol is found in the alcohol fraction, this is counted as 2 moles of carbon. If 4 moles of CO had been converted to products other than CO$_2$, the one mole of ethanol would result in ethanol being yielded at 50 carbon mole percent. Carbon dioxide and water are not counted as products in this calculation.

The first component of the catalyst preferably consists essentially of at least one element selected from the group consisting of molybdenum and tungsten in free or combined form. Molybdenum is preferred.

The first component of the catalyst may be present in the catalyst in "free or combined form" which means that it may be present as a metal, an alloy or a compound of the element. Representative compounds include the sulfides, carbides, oxides, halides, nitrides, borides, salicylides, oxyhalides, carboxylates such as acetates, acetyl acetonates, oxalates, etc., carbonyls, and the like. Representative compounds also include the elements in anionic form such as molybdates, phosphomolybdates, tungstates, phosphotungstates, and the like, and include the alkali, alkaline earth, rare earth and actinide series salts of these anions. The sulfides, carbonyls, carbides and oxides are preferred with the sulfides being most preferred.

The molybdenum or tungsten may be present in an amount based on the weight of the total catalyst of at least about two percent, preferably at least about 5 percent with an upper limit of about 70 percent and preferably about 30 percent of the total catalyst.

The first and second components may be generally present as the sulfide. It is not necessary for the practice of this invention that any particular stoichiometric sulfide be present, only that the first and second components may be present in combination with sulfur. Some of the first or second component may be present in combination with other elements such as oxygen or as oxysulfides.

The second component of the catalyst preferably consists essentially of at least one element selected from the group consisting of iron, cobalt or nickel in free or combined form. Cobalt and nickel are preferred. Because of the possiblity of the formation of nickel tetracarbonyl, cobalt is most preferred.

The second component of the catalyst may be present in the catalyst in "free or combined form" which means that it may be present as a metal, an alloy or a compound of the element. Representative compounds include the sulfides, carbides, oxides, halides, nitrides, borides, salicylides, oxyhalides, carboxylates such as acetates, acetylacetonates, oxalates, etc., carbonyls, and the like. Representative compounds also include the elements combined with first component elements in anionic form such as iron, cobalt or nickel molybdates, phosphomolybdates, tungstates, phosphotungstates, and the like. The sulfides, carbonyls, carbides and oxides are preferred with the sulfide being most preferred.

The iron, cobalt or nickel or mixtures thereof may be present in an amount based on the weight of the total catalyst of at least about two percent, preferably at least about 5 percent with an upper limit of about 70 percent and preferably about 30 percent of the total catalyst.

The first and second components may be present in the finished catalyst in an atomic ratio of about 1:10 to about 10:1. Preferably the first and second components are present in a ratio of from about 1:4 to about 4:1. With a coprecipitated Mo/Co sulfide catalyst an atomic ratio of Mo/Co of about 2:1 yields about a 1:5 weight ratio of methanol to C$_2$–C$_5$ alcohols and an atomic ratio of about 3:1 yields a weight ratio of about 1:3 methanol to C$_2$–C$_5$ alcohols.

The third component which is a promoter may consist essentially of one or more alkali elements or alkaline earth elements in free or combined form. Alkali elements include lithium, sodium, potassium, rubidium and cesium. Alkaline earth elements include: beryllium, magnesium, calcium, strontium and barium. Alkali elements and in particular, cesium and potassium, are preferred. Potassium is most preferred.

The promoter may be present in free or combined form as a metal, oxide, hydroxide, carbonate, sulfide or as a salt or a combination of these. The alkaline promoter is preferably present at a level sufficient to render the supported catalyst or the bulk catalyst more basic. The promoter is generally present in an amount of at least about 0.05 weight percent as a free element in the finished catalyst. Preferably it is present in an amount of at least about 0.5 percent and most preferably at least 2.0 percent. Large amounts up to about 30 percent of the promoter may be present. Preferably the promoter is present at less than 20 percent.

The promoter may be added as an ingredient to the other components or to the support or may be part of one of the other components such as sodium or potassium molybdate or as an integral part of the support. For example, carbon supports prepared from coconut shells often contain small amounts of alkali metal oxides or hydroxides or the support may contain a substantial amount of the promoter such as when the support is magnesia.

A fourth optional component of the catalyst is a support which may assume any physical form such as pellets, granules, beads, extrudates, etc. The supports may be coprecipitated with the active metal species, or the support in powder form may be treated with the active metal species and then used as is or formed into the aforementioned shapes, or the support may be formed into the aforementioned shapes and then treated with the active catalytic species.

The first three components may be dispersed on the support by methods known in the art. Examples include: impregnation from solution followed by conversion to the active species, vapor deposition, intimate physical mixing, sulfiding of other first or second component species, precipitation of sulfides in the presence of the support and the like. One or more of these methods may be used.

One alternative method of placing the first three components on the support is known as the incipient wetness technique. Water- or solvent-soluble salts of the metals to be dispersed on the support are chosen. The soluble salts which may be a single salt or more than one salt are dissolved in a quantity of solvent which may be aqueous, nonaqueous or a mixed solvent. A sufficient quantity of the resulting solution is added to the support in an amount no more than will be completely absorbed by the support. The solvent is then evaporated to leave the salt dispersed on the support. Depending on the solubility of the salt chosen and on the quantity of the element desired to be dispersed on the support, this process may be performed once or several times. Impregnations with two or more species may be performed by codissolving them in the solvent or by adding them separately in different quantities or types of solvent. If the species loaded on the support is not the desired one, the loaded support may be treated to convert it to the desired species. For example, oxides may be reduced, with reducing agents such as hydrogen; salts may be decomposed for example by heating, for example, the decomposition of $(NH_4)_2MoS_4$ or $MoS_3$ to $MoS_2$; or one species may be converted to another by contact with a chemical agent, for example sulfiding. A catalyst may be sulfided by contact with a sulfur-containing agent such as $H_2S$.

Preferred methods of placing the first or second components on a support include, for example, impregnation with $(NH_4)_2MoS_4$ followed by decomposition with heat; precipitation of sulfides of the first and/or second components in contact with the support. Placing of the sulfided first and second components on a support is preferably followed by treatment with $H_2$ at elevated temperatures, usually with 20–50 ppm $H_2S$ present.

Exemplary support materials include: the aluminas, basic oxides, the silicas, carbons, or suitable solid compounds of magnesium, calcium, strontium, barium, scandium, yttrium, lanthanum and the rare earths, titanium, zirconium, hafnium, vanadium, niobium, tantalum, thorium, uranium, and zinc. Oxides are exemplary compounds. Preferably the supports are neutral or basic or may be rendered neutral or basic by addition of the alkaline promoters. The aluminas include the alpha, gamma, and eta types. The silicas include for example, silica gel, diatomaceous earth, and crystalline silicates.

The carbon supports, which are preferred supports, include activated carbons such as those prepared from coals and coal-like materials, petroleum-derived carbons and animal- and vegetable-derived carbons. Preferably the carbon support will have a surface area of 1–1500 $m^2/g$, more preferably 10–1000 $m^2/g$ and most preferably 100–500 $m^2/g$ as measured by the BET nitrogen test. Preferably, micropores (<20 Å (<2 nm)) are minimized and at least twenty percent of the volume of the pores comprises pores having a diameter of from about 20 Å to about 600 Å (2–60 nm). Examples include coconut shell charcoal, coals, petroleum cokes, carbons formed by pyrolyzing materials such as vinylidene chloride polymer beads, coal, petroleum coke, lignite, bones, wood, lignin, nut shells, petroleum residues, charcoals, etc.

Based upon the weight of the total catalyst, the support when present generally comprises at least about 20 percent of the catalyst and generally not more than about 96 percent of the catalyst. Preferably the support comprises at least about 50 weight percent and most preferably at least about 70 weight percent of the catalyst.

For several reasons the preferred form of the catalyst is the agglomerated sulfide. Certain forms of cobalt-/molybdenum sulfide are more preferred. Most preferred is agglomerated, cobalt/molybdenum sulfide in which the cobalt and molybdenum sulfides are coprecipitated.

Methods for making sulfide catalysts are disclosed generally at pages 23–34 of *Sulfide Catalysts Their Properties and Applications,* O. Weisser and S. Landa, Pergamon Press, New York, 1973, the whole which is incorporated herein by reference.

Sulfide catalysts may be made by precipitating iron, cobalt or nickel sulfide in the presence of ammonium tetrathiomolybdate or other thiomolybdates, or thiotungstates and thereafter thermally treating the mixture to convert the thiomolybdate or thiotungstate salt to the sulfide; or as disclosed in U.S. Pat. No. 4,243,553 and U.S. Pat. No. 4,243,554 which are hereby incorporated by reference; or from purchased active combined first and second component sulfides.

Cobalt and molybdenum may be impregnated as salts on a support, then calcined to the oxide and then sulfided with $H_2S$ as taught in GB Patent publication 2,065,491 which is incorporated herein by reference. A cobalt/molybdenum sulfide may also be precipitated directly on to a support, but the unsupported cobalt-/molybdenum sulfide is preferred. Other combinations of first and second component sulfides may be similarly made.

An unsupported catalyst preferably has a surface area of at least 10 $m^2/g$ and more preferably more than 20 $m^2/g$ as measured by the BET nitrogen surface area test.

A preferred method of making a cobalt/molybdenum sulfide or other first and second component sulfide is by adding solutions of ammonium tetrathiomolybdate or other equivalent salt and a cobalt or nickel salt such as the acetate more or less simultaneously to 30 percent acetic acid. This results in the coprecipitation of cobalt-/molybdenum sulfide. By varying the ratios of cobalt and molybdenum or other salts in the solutions one may vary the ratio of cobalt and molybenum or other elements in the sulfide catalyst. The cobalt/molybdenum sulfide or other sulfide may then be separated from the solvent, dried and blended with a third component promoter such as $K_2CO_3$ and agglomerating agents and/or pelleting lubricants, then pelleted and used as the catalyst in the process.

The alkali or alkaline earth promoter may be added to the active catalytic elements prior to, during or after the formation of the sulfide by physical mixing or solution impregnation. The active metal sulfide may then be combined with binders such as bentonite clay, and/or pelleting lubricants such as Sterotex ® and formed into shapes for use as a catalyst.

The finished catalyst may be used in a fixed bed, moving bed, fluid bed, ebullated bed or a graded bed wherein concentration and/or activity of the catalyst varies from inlet to outlet in similar manner to known catalysts. The catalyst may be used in powdered form or may be formed into shapes with or without a binder.

Catalysts of the invention preferably contain less than 25 weight percent, based on the total weight of carbon oxide hydrogenation active metals, of other carbon oxide hydrogenation active metals and more preferably less than 20 weight percent and most preferably less than 2 weight percent. The inventive catalyst may be essentially free of other carbon oxide hydrogenating components. By essentially free it is meant that other carbon oxide hydrogenating components do not significantly alter the character or quantity of the alcohol fraction. For example, a significant change would be a five percent change in the amount of the alcohol fraction or a five percent change in the percentage of any alcohol in the alcohol fraction.

Carbon oxide hydrogenating components present in thus limited quantities or excluded are preferably those that contain chromium, manganese, copper, zinc, ruthenium and rhodium. More preferably, in addition to the above-mentioned components, those that contain: halogen, titanium, vanadium, cerium, thorium, uranium, iridium, palladium, platinum, silver and cadmium are excluded.

Under preferred conditions the catalyst is stable for long periods of time and under ideal conditions may be stable and active for as many as 6000 hours or more. Activity and selectivity are preferably substantially retained after 700 hours of operation, more preferably after 2000 hours and most preferably after 4000 hours operation. In the case of reduced oxide catalysts, declines in activity and selectivity may generally be regenerated by reduction with hydrogen after which the catalyst may regain most of its original activity and be used for another long period of time before regenerating again.

The catalysts are generally not adversely affected by up to 100 ppm sulfur in the $H_2/CO$ feed. However, no advantage is realized by the presence of sulfur, and generally sulfur must be removed from the mixed alcohols fraction. Accordingly, low sulfur levels in the feed are preferred.

At the conditions described above, the process yields substantial quantities of alcohols. Under preferred conditions, the weight units per hour of alcohols boiling in the range of motor gasoline per weight unit of catalyst may exceed 0.2. Under certain conditions, it may exceed 1.0 and may reach 1.4.

The alcohol fraction formed at greater than a 20 percent $CO_2$ free carbon selectivity boils in the motor gasoline range. The minimum boiling pure alcohol is methanol at 64.7° C. ASTM D-439 calls for a 225° C. endpoint for automotive gasoline. Accordingly the alcohol fraction formed at greater than a 20 percent $CO_2$ free carbon selectivity may boil in the range of from about 60° C. to about 225° C. when distilled by ASTM D-86. Other alcohols may boil outside this range but preferably do not. It is not necessary that the entire liquid product boil in this range, but it is preferred. It is not necessary that the alcohol fraction meet all the distillation specifications for motor gasolines—only that it boil within the broad range of motor gasolines. For example, it need not be within 50 percent evaporated limits as set by ASTM D-439. Only 20 carbon mole percent of the total $CO_2$ free product must be alcohols that boil in this range. The alcohol fraction formed may be used as a motor fuel blending stock. Preferably, the alcohol fraction formed will have a research octane blending value in motor gasoline of greater than about 100, more preferaby greater than about 110 and most preferably greater than about 120.

Preferably, a $C_1-C_8$ alcohol fraction is formed in at least about 20 percent $CO_2$ free carbon selectivity and most preferably a $C_1-C_5$ alcohol fraction is formed in at least about 20 percent $CO_2$ free carbon selectivity.

The $C_1-C_5$ alcohol fraction may contain methanol, ethanol, 1-propanol, 1-butanol, 2-methyl-1-propanol, 1-pentanol, 2-methyl-1-butanol, but doesn't generally contain substantial tertiary alcohols. In addition to these named alcohols the $C_1-C_8$ alcohol fraction may contain the $C_6-C_8$ alcohols wherein the hydroxyl group may be attached to a carbon which is attached to one or two other carbon atoms.

The process for making mixed alcohols may yield a lower ratio of $C_1$ to $C_2-C_5$ alcohols in the alcohol fraction with the combination of the first, second and third components and optionally the fourth component listed above than with a catalyst containing the same first, third and optional fourth component but not the second component. With just the first, third and optional fourth component, and absent addition of a sulfur, releasing substance a typical $C_1$ to $C_2-C_5$ weight ratio may be 1.1 or more. With the catalyst of the invention the $C_1$ to $C_2-C_5$ weight ratio may be less than one, preferably is less than about 0.8, more preferably less than about 0.5 and most preferably less than about 0.4 and can even be about 0.25 or lower.

Primarily the $C_2-C_5$ alcohol that increases is ethanol. The weight percentage of ethanol made without the second component in the catalyst is typically less than 25 percent of the total $C_1-C_5$ alcohols. In the presence of an iron-, cobalt- or nickel-containing catalyst of the same character otherwise, the ethanol may be greater than 25 weight percent, preferably greater than 30 weight percent and most preferably greater than 40 weight percent of the $C_1-C_5$ alcohol fraction.

The catalysts of the invention preferably contain the first component and second component in an atomic ratio of less than about 5:1. Preferably, the atomic ratio is less than 3:1 and most preferably about 2:1 or less.

Coprecipitated cobalt/molybdenum sulfide is the preferred combination of the first and second components. The sulfur content may or may not be stoichiometric as their are many sulfides of these two metals.

Under preferred conditions, the amount of water formed is substantially less than the amount of alcohols formed. Typically there is less than 20 weight percent and preferably less than 10 weight percent water based on the quantity of alcohol. This water may be removed by known techniques if the alcohol fraction is to be used as a motor fuel additive. If the water content is about two weight percent or less based on alcohols, the water may advantageously be removed by absorption on molecular sieves. At higher water contents one may use a water gas shift drying step as disclosed in British Patent Publications 2,076,015 and 2,076,423; or U.S. Application No. 508,625, filed June 28, 1983. These references are hereby incorporated herein by reference. A water gas shift catalyst tolerant to sulfur, and alcohol catalyst carry over should be used in the drying step. Halder Topsoe SSK is exemplary.

The product mixture, as formed under preferred conditions, contains only small portions of other oxygenated compounds besides alcohols. These other compounds may not be deleterious to using the product, as is, in motor fuels.

In all cases, the alcohol fraction is formed in at least about 20 percent $CO_2$ free carbon selectivity. Preferably the alcohol fraction is formed in at least about 30 percent $CO_2$ free carbon selectivity, more preferably greater than about 50 percent and ideally can be greater than about 70 percent.

Preferably the co-products formed with the alcohol fraction are primarily gaseous products. That is $C_1-C_4$ hydrocarbons. By hydrocarbons, it is meant that heteroatoms such as oxygen, sulfur and nitrogen are not present in the molecule. Preferably $C_5+$ hydrocarbons are coproduced at less than about 20 percent $CO_2$ free carbon selectivity, more preferably at less than 10 percent and most preferably at less than 5 percent. Lower amounts of normally liquid hydrocarbons make the normally liquid alcohols easier to separate from by-products.

Generally, alcohol selectivity may be increased by increasing pressure, space velocity product gas recycle ratio and by decreasing $H_2/CO$ feed ratio and temperature.

CATALYSTS

Comparison A

A solution of 180 g of $(NH_4)_6Mo_7O_{24}4H_2O$ in 500 $cm^3$ of water containing 100 $cm^3$ of concentrated $NH_4OH$ reacts with a small excess of $(NH_4)_2S$ (about 1300 $cm^3$ of 22 percent $(NH_4)_2S$ in water). The reaction mixture is stirred at 60° C. for one hour and evaporated to dryness at 60°–70° C. A portion of the resulting $(NH_4)_2MoS_4$ is calcined at 500° C. for one hour in an inert atmosphere such as nitrogen to form $MoS_2$. The resulting $MoS_2$ powder (6.6 g) is mixed with 2.0 g of bentonite clay, 1.0 g of $K_2CO_3$ and 0.4 g of a pelleting lubricant (Sterotex ®) by grinding in a mortar and pestle. The product is used to make alcohols in the unpelleted powder state. No pretreatment of the catalyst is performed.

EXAMPLE 1

A 10.0-g portion of the $MoS_2$ from Comparision A is mixed in a mortar and pestle with 8.4 g $Co(CH_3CO_2)_24H_2O$ (cobalt acetate) and water sufficient to yield a thick paste. The paste is dried at 60° C. and calcined at 500° C. for one hour in an inert gas such as nitrogen to give a black powder with a Mo/Co atomic ratio of about 3:1.

Similar to Comparison A, 6.6 g of this powder are mixed with 2.0 g bentonite clay, 1.0 g of $K_2CO_3$ and 0.4 g of Sterotex ® in a mortar and pestle. This catalyst is used in unpelleted powder form and is not pretreated.

EXAMPLE 2

A coprecipitated cobalt/molybdenum sulfide is prepared with a Mo/Co atomic ratio of about 2:1. Fifteen grams of $(NH_4)_6Mo_7O_{24}4H_2O$ (0.085 moles Mo) is dissolved in 106 $cm^3$ of 22 percent $(NH_4)_2S$ in water and stirred at 60° C. for one hour to form $(NH_4)_2MoS_4$. A solution of 10.5 g of $Co(CH_3CO_2)_2$ (0.042 mole Co) in 200 $cm^3$ of water is prepared.

The two solutions are added simultaneously, dropwise to a stirred solution of 30 percent aqueous acetic acid in a baffled flask at 50° C. over a one-hour period. After stirring for one additional hour the reaction mix is filtered and the filter cake dried at room temperature and then calcined for one hour at 500° C. in an inert atmosphere such as nitrogen. Similar to Example 1, 6.6 g of the calcined cobalt/molbdenum sulfide is ground together with 2.0 g of bentonite clay, 1.0 of g $K_2CO_3$ and 0.4 g of Sterotex ® lubricant in a mortar and pestle. This catalyst is used in unpelleted, powder form without pretreatment.

EXAMPLE 3

This Example discloses the making of a coprecipitated cobalt/molbdenum sulfide with a Mo/Co atomic ratio of about 3:1.

The coprecipitated cobalt/molbdenum sulfide is prepared using the same procedure as Example 2 except that 7.1 g of $Co(CH_3CO_2)_2.4H_2O$ (0.28 moles Co) is used. This catalyst is used in unpelleted, powder form without pretreatment.

EXAMPLE 4

This Example discloses the use of a commercially available alkalized molybdenum/cobalt catalyst, Haldor Topsoe SSK, and available from Haldor Topsoe A/S of Denmark.

EXAMPLE 5

This Example discloses the use of an alkalized Mo/Ni sulfide having a Mo/Ni atomic ratio of about 2:1.

Seventy-five grams (0.425 mole) of $(NH_4)_6Mo, O_{24}.H_2O$ is dissolved in 530 $cm^3$ of 22 percent aqueous $(NH_4)_2S$ at 60° C.–70° C. with stirring for one hour to give a solution of $(NH_4)_2MoS_4$. A second solution containing 53 g of nickel acetate (0.212 mole Ni) in 500 $cm^3$ of water is prepared. These two solutions are added dropwise over a 40-minute period to one liter of vigorously stirred 30 percent acetic acid. After stirring for one additional hour at 60° C., the resulting slurry is filtered. The black filter cake is washed with water and dried overnight at 100° C. under nitrogen. The dry filter cake is calcined under nitrogen at 500° C. for one hour. Similarly to Example 1, 6.6 g of the calcined Mo/Ni sulfide is ground with mortar and pestle with 2 g of bentonite clay, 1 g of $K_2CO_3$ and 0.4 g of Sterotex ® pelleting lubricant. The catalyst is used in unpelleted powder form without pretreatment. Results are shown in the Table.

EXAMPLE 6

This Example discloses the use of a Mo/Fe sulfide made by coprecipitation.

A barium acetate solution, prepared by dissolving 12.2 g (0.071 mole) of $Ba(OH)_2$ in 100 $cm^3$ of water containing 10 $cm^3$ of glacial acetic acid, is mixed with 100 $cm^3$ of aqueous solution containing 19.7 g (0.071 mole) of $FeSO_4$. The resulting precipitate was filtered off under nitrogen and discarded, leaving a solution of ferrous acetate. A solution of $(NH_4)_2MoS_4$ (0.142 mole) is prepared by dissolving 25 g of $(NH_4)_6Mo_7O_{24}.4H_2O$ in 180 $cm^3$ of 22 percent aqueous $(NH_4)_2S$ and stirring at 60° C. for one hour. The solutions of ferrous acetate and ammonium tetrathiomolybdate are added simultaneously over a 30-minute period to a vigorously stirred solution of 75 $cm^3$ of glacial acetic acid in 225 $cm^3$ of water at 60° C. The resulting black slurry is stirred at 60° C. for one hour and filtered. The black filter cake is washed, dried at 110° C. overnight under nitrogen, and calcined at 500° C. under nitrogen for one hour. The calcined Mo/Fe sulfide is blended in a mortar and pestle with bentonite clay, $K_2CO_3$ and Sterotex ® to give a formulation containing 66 percent Mo/Fe sulfide, 20 percent clay, 10 percent $K_2CO_3$ and 4 percent Sterotex ®. This catalyst (5 $cm^3$) is combined with 5 $cm^3$ of tabular alumina and loaded into the reactor.

Preparation of Alcohols

In the general method of these Examples, the reactor consists of a one-half inch (1.27 cm) stainless steel tube packed with catalyst. The total volume of catalyst is about 6 $cm^3$. Premixed hydrogen, carbon monoxide, and nitrogen feed gases from cylinders are compressed and regulated at the pressures stated in the table. The feed gas mixture contains hydrogen and carbon monoxide at the stated molar ratios and about five percent by volume of nitrogen serving as an internal standard. About 50 ppm of $H_2S$ is also present in the feed gas.

The mixed feed gas passes through the bed of activated carbon at room temperature to remove iron and other carbonyl contaminants. The feed gas then passes at the stated hourly space velocities through the fixed bed reactor which is maintained at the stated reaction temperatures by an electric air recirculated oven and which is held at 1500 psig (10.45 MPa). The reactor effluent passes through a gas liquid separator at ambient temperature and the reaction pressure stated in series with a dry ice trap at ambient pressure. Both gas and liquid phases are analyzed to give the results in Table I.

TABLE I

| Example | A | 1 | 2 | 3 |
|---|---|---|---|---|
| Temp. (°C.) | 265 | 295 | 305 | 295 |
| $H_2/CO$ (molar ratio) | 1.04 | 0.98 | 0.98 | 0.98 |
| GHSV ($hr^{-1}$) | 1200 | 2200 | 1300 | 1050 |
| CO Conversion (%) | 33.1 | 10.3 | 39.0 | 29.2 |
| Wt. Units CO converted per wt. unit of catalyst per hr | 0.19 | 0.12 | 0.23 | 0.13 |
| $CO_2$ produced[1] (%) | 31.3 | 18.6 | 33.5 | 31.3 |
| Selectivities[2] (%) | | | | |
| Gas Phase | | | | |
| $CH_4$ | 20.2 | 7.0 | 12.6 | 11.3 |
| $C_2+$ hydrocarbons | 4.3 | 3.2 | 5.7 | 3.2 |
| Subtotal | 24.5 | 10.2 | 18.2 | 14.5 |
| Liquid Phase | | | | |
| Methanol | 32.3 | 37.8 | 16.1 | 22.7 |
| Ethanol | 31.8 | 29.5 | 39.9 | 40.7 |
| Propanols | 7.7 | 7.8 | 14.9 | 12.7 |
| Butanols | 1.6 | 5.3 | 4.3 | 3.5 |
| Pentanols | 0.2 | 2.4 | 0.5 | 1.2 |
| Subtotal | 73.6 | 82.8 | 75.7 | 80.8 |
| Weight Ratio | | | | |
| $C_1/C_2$–$C_5$ alcohols | 1.13 | 1.24 | 0.39 | 0.57 |
| Other oxygenates[3] and hydrocarbons | 1.9 | 7.0 | 6.0 | 4.7 |
| $H_2O$[4] (wt. %) | 2.7 | 1.4 | 1.8 | 2.3 |

| Example | 4 | 5 | 6 |
|---|---|---|---|
| Temp. (°C.) | 350 | 300 | 321 |
| $H_2/CO$ (molar ratio) | 1.02 | 1.03 | 1.04 |
| GHSV ($hr^{-1}$) | 614 | 1330 | 1480 |
| CO Conversion (%) | 12.7 | 33.1 | 27.1 |
| Wt. units CO converted per wt units of catalyst per hr | 0.04 | 0.26 | 0.27 |
| $CO_2$ produced[1] (%) | 40.1 | 32.9 | 36.9 |
| Selectivities[2] (%) | | | |
| Gas Phase | | | |
| $CH_4$ | 21.7 | 18.0 | 7.4 |
| $C_2+$ hydrocarbons | 4.9 | 2.7 | 16.7 |
| Subtotal | 26.6 | 20.7 | 24.1 |
| Liquid Phase | | | |
| Methanol | 17.7 | 15.2 | 6.9 |
| Ethanol | 15.2 | 41.8 | 21.0 |
| Propanols | 16.7 | 11.5 | 17.9 |

TABLE I-continued

| Butanols | 10.9 | 1.4 | 10.8 |
|---|---|---|---|
| Pentanols | 5.0 | 1.5 | 7.1 |
| Subtotal | 65.5 | 71.4 | 63.7 |
| Weight Ratio | | | |
| $C_1/C_2$–$C_5$ alcohols | 0.60 | 0.39 | 0.19 |
| Other oxygenates[3] and hydrocarbons | 7.9 | 7.9 | 12.2 |
| $H_2O$[4] (wt. %) | 4.6 | 1.9 | 6.7 |

[1]100 × moles of $CO_2$ formed for each mole of CO converted in the reactor.
[2]Selectivities, except for $CO_2$, are based on carbon mole selectivity on a $CO_2$ free basis.
[3]Assumed a carbon number of 4 for other oxygenates.
[4]Water is calculated as weight percent of the liquid phase.

Although the invention has been described in considerable detail, it must be understood that such detail is for the purpose of illustration only and that many variations and modifications can be made by one skilled in the art without departing from the spirit and scope of the invention.

What is claimed is:

1. A process for making alcohols comprising contacting a mixture of hydrogen and carbon monoxide with a catalyst comprising:
   (1) as a first component, molybdenum sulfide;
   (2) as a second component, iron sulfide;
   (3) as a third component, a promoter comprising an alkali or alkaline earth element in free or combined form, said catalyst excluding rhodium, copper and ruthenium; at a pressure of at least about 500 psig and at conditions sufficient to form an alcohol fraction boiling in the range of motor gasoline in at least 50 percent $CO_2$ free carbon selectivity, said alcohol fraction containing a $C_1$ to $C_{2-5}$ alcohol weight ratio of less than about 1:1.

2. The process of claim 1 wherein the mixture of hydrogen and carbon monoxide contains a molar ratio of $H_2/CO$ of less than about 2:1.

3. The process of claim 1 wherein the alcohol fraction contains a $C_1$ to $C_2$–$C_5$ alcohol weight ratio of less than about 0.8:1.

4. The process of claim 3 wherein the alcohol fraction contains a $C_1$ to $C_2$–$C_5$ alcohol weight ratio of less than about 0.5:1.

5. The process of claim 1 wherein the atomic ratio of the first component to the second component is from about 1:4 to about 4:1.

6. The process of claim 5 wherein the atomic ratio of the first component is from about 3:1 to about 1:1.

7. The process of claim 6 where in the first and second components are present as coprecipitated sulfides.

8. The process of claim 1 wherein a ratio of methanol to $C_2$–$C_5$ alcohols is lower than a process in which all the conditions are the same except that the catalyst does not contain the second component.

9. The process of claim 1 wherein chromium, manganese and zinc are excluded from the catalyst.

10. The process of claim 9 wherein halogen, titanium, vanadium, cerium, thorium, uranium, iridium, palladium, platinum, silver and cadmium are excluded from the catalyst.

* * * * *